(12) United States Patent
Kim et al.

(10) Patent No.: US 8,828,445 B2
(45) Date of Patent: Sep. 9, 2014

(54) METHOD FOR PREPARING NANO-PARTICLES UTILIZING A SACCHARIDE ANTI-COAGULANT

(75) Inventors: Kab Sig Kim, Seoul (KR); Joo Won Park, Seoul (KR)

(73) Assignee: Bio-Synectics Inc., Seoul (KR)

( * ) Notice: Subject to any disclaimer, the term of this patent is extended or adjusted under 35 U.S.C. 154(b) by 0 days.

(21) Appl. No.: 13/635,717

(22) PCT Filed: Mar. 22, 2011

(86) PCT No.: PCT/KR2011/001956
§ 371 (c)(1),
(2), (4) Date: Sep. 18, 2012

(87) PCT Pub. No.: WO2011/118960
PCT Pub. Date: Sep. 29, 2011

(65) Prior Publication Data
US 2013/0005643 A1 Jan. 3, 2013

(30) Foreign Application Priority Data
Mar. 22, 2010 (KR) .................. 10-2010-0025486

(51) Int. Cl.
*A61K 9/50* (2006.01)
(52) U.S. Cl.
USPC ........................................................ 424/501
(58) Field of Classification Search
CPC ................................ A61K 9/14; A61K 9/1652
See application file for complete search history.

(56) References Cited

U.S. PATENT DOCUMENTS

| | | | |
|---|---|---|---|
| 5,145,684 A | 9/1992 | Liversidge et al. | |
| 5,202,129 A | 4/1993 | Samejima et al. | |
| 5,302,401 A | 4/1994 | Liversidge et al. | |
| 5,534,270 A * | 7/1996 | De Castro | 424/490 |
| 6,316,030 B1 | 11/2001 | Kropf et al. | |
| 6,352,737 B1 | 3/2002 | Dolhaine et al. | |
| 6,368,620 B2 | 4/2002 | Liu et al. | |
| 6,592,903 B2 | 7/2003 | Ryde et al. | |
| 6,596,206 B2 | 7/2003 | Lee | |
| 6,630,121 B1 | 10/2003 | Sievers et al. | |
| 2002/0168402 A1 | 11/2002 | Kipp et al. | |
| 2003/0104068 A1 | 6/2003 | Mathiowitz et al. | |
| 2003/0185869 A1 | 10/2003 | Wertz et al. | |
| 2004/0067251 A1 | 4/2004 | Johnston et al. | |
| 2006/0073203 A1 | 4/2006 | Ljusberg-Wahren et al. | |

FOREIGN PATENT DOCUMENTS

| | | |
|---|---|---|
| JP | 2010-500340 A | 1/2010 |
| KR | 10-2005-0054819 A | 6/2005 |
| KR | 10-2007-0107841 A | 11/2007 |
| KR | 10-2007-0107879 A | 11/2007 |
| KR | 10-2008-0017161 A | 2/2008 |
| WO | WO 00/37169 | 6/2000 |

(Continued)

OTHER PUBLICATIONS

Lachman, et al., "The Theory and Practice of Industrial Pharmacy," Chapter 2, "Milling," 1986, p. 45.

(Continued)

*Primary Examiner* — Carlos Azpuru
(74) *Attorney, Agent, or Firm* — Clark G. Sullivan; Troutman Sanders LLP (57) ABSTRACT

The present invention relates to a method for preparing nano-particles, and more particularly, to a method for preparing nano-particles containing active materials in a simple and highly efficient manner through a grinding process.

10 Claims, 6 Drawing Sheets

(56) References Cited

FOREIGN PATENT DOCUMENTS

| WO | WO 02/38127 A2 | 5/2002 |
| WO | WO 2008/062429 A2 | 5/2008 |
| WO | WO 2008/126797 | 10/2008 |

OTHER PUBLICATIONS

Mochalin, Vadym N., et al., "Manufacturing Nanosized Fenofibrate by Salt Assisted Milling," Pharmaceutical Research, Jun. 2009, vol. 26, No. 6, pp. 1365-1370.

Yamamoto, Keiji, et al., "Preparation of Drug Nanoparticles by Co-grinding with Cyclodextrin: Formation . . . ," Chem. Pharm. Bull., Mar. 2007, 55(3), pp. 359-363.

Tom, Jean W., et al., "Formation of Bioerodible Polymeric Microspheres and Microparticles by Rapid Expansion of Supercritical . . . ," Biotechnol. Prog., 1991, 7(5), pp. 403-411.

Debenedetti, Pablo G., et al., "Application of supercritical fluids for the production of sustained delivery devices," J. Control. Release, 1993, 24, pp. 27-44.

International Search Report, PCT/KR2011/001956, Nov. 30, 2011.

\* cited by examiner

METHOD FOR PREPARING NANO-PARTICLES UTILIZING A SACCHARIDE ANTI-COAGULANT

TECHNICAL FIELD

The present invention relates to a method for preparing nanoscale particles of active material. More specifically, the present invention relates to a method for preparing nanoparticle powder of active ingredient by uniformly mixing saccharide as an anti-coagulation agent; biocompatible polymer and/or surfactant; and active ingredient in the presence of water, drying the mixture, and grinding the dried mixture, or by making nanoparticles of saccharide as an anti-coagulation agent with biocompatible polymer and/or surfactant, uniformly mixing the nanoparticles with active ingredient, and grinding the mixture.

BACKGROUND ART

A demand for a technique of an effective and rapid preparation of very fine particles in regular size has been constantly required in various industrial fields. Such fine particles in regular size have many advantages, particularly among which good flowability and little deviation in particle interaction are very advantageous in industrial application. For example, in drug industry, the particle size of a therapeutic agent greatly affects to the dissolution rate, bioavailability, formulation and the like, and as the deviation in the interaction between the particles of a therapeutic agent becomes smaller, the overall stability of the therapeutic agent becomes better.

In medicinal products, if the particle of a therapeutic agent is made into nanoscale size, the following advantages are obtained. First of all, for drugs having a small enteral absorption rate in oral administration, more absorption can be achieved and thus the bioavailability of the therapeutic agent can be increased, as compared with those of a bigger size. Furthermore, the dosage form of drugs can be various. For instance, a drug that has been administered only via oral route may be administered by inhalation. In a controlled-release drug formulation, the release rate of a therapeutic agent is a very important factor. When the particle size of the therapeutic agent is formed in nanoscale, the particle size becomes relatively more uniform, thus the release rate can become more expectable, thereby being possible to provide more effective therapeutic agent.

In order to take various advantages of uniform nanoparticles as described above, many attempts have been made to prepare an active ingredient as a nanoparticle. For this object, mechanical techniques such as crushing, grinding, milling and the like have been conventionally employed to make relatively large particles smaller. Recently in the pharmaceutical industry, a method using an air-jet mill for milling a large amount of drugs to the size range being suitable for medicinal or pharmaceutical use has been commonly used. However, according to U.S. Pat. No. 5,534,270 and Lachman, et al. [The Theory and Practice of Industrial Pharmacy, Chapter 2, "Milling", p. 45, (1986)], such conventional mechanical processes have been generally recognized as having a limitation of possible minimum particle size of about tens of micrometers.

It was reported that nano-scale fenofibrate was obtained by a method comprising mixing fenofibrate and sodium chloride (weight ratio of 1:7) using ball mill and dry-grinding the mixture using an attritor mill [Vandym N. Mocahlin et al., Pharmaceutical Reserch, Vol. 26, No. 6, 1365~1370. June 2009], wherein sodium chloride is a very hard material and when it is ground by ball mill, it serves as grind media and at the same time, it prevents re-coagulation of the ground fenofibrate. Furthermore, in WO 2008/126797, Hirokawa, Takashi et al. disclose a process for providing nano-scale active ingredient by mixing sodium chloride and polyol compound with active ingredient and then subjecting it to wet-milling process without grinding media. However, these processes use excessive sodium chloride and thus essentially require a step for removing sodium chloride in order to use the obtained nanoparticle in medicinal products U.S. Pat. No. 5,202,129 discloses a method for preparing fine particles of a poorly water-soluble drug by mixing the drug with 2.5 times or more of low molecular weight saccharide or sugar alcohol and then dry-grinding the mixture. However, this method has a problem that because a large amount of saccharide is used, for actual use in medicinal products, it is required to remove the saccharide by dispersing the ground mixture in water, filtering the dispersed mixture and drying the filtered mixture.

Keiji Yamamoto et al. asserted that nanoparticles of drug may be prepared by grinding the drug along with cyclodextrin using a rod mill [Chem, Pharm, Bull. 55(3)359-363 (2007)]. They asserted that the amount of cyclodextrin used in this method is about two times of active ingredient in molar ratio, i.e. about four times in weight ratio, and that humidity for hydrating all used cyclodextrin is needed and it is disadvantageous if the humidity is too high or too low.

U.S. Pat. No. 5,145,684 discloses a method for preparing particles of a poorly water-soluble drug in a size of hundreds of nanometers by wet-milling the poorly water-soluble drug in the presence of a surfactant. This technique should be applied after preparing the drug in a particle size of 100 micrometers or less by using a conventional milling process. In this method, the time for preparing particles within the target size range depends on the mechanical device used therefor. When a ball mill is used, 5 days or longer is required. However, when a high shear media mill is used, the particles can be prepared within 1 day. However, since the nanoparticle obtained in this method is in liquid phase, in order to make it in powder type, a process of spray dry or freeze dry should be conducted. During the drying process, however, coagulation of particles occurs and when the obtained powder is re-dispersed in liquid, it is difficult to obtain a dispersion of particles in nanometer scale. In order to solve such problem, U.S. Pat. No. 5,302,401 discloses an anti-coagulation agent employed during lyophilization. Additionally, U.S. Pat. No. 6,592,903 B2 discloses use of a stabilizer, a surfactant and an anti-coagulation agent during a spray dry process. Furthermore, US Patent Application Publication No. 2003/0185869 A1 discloses an application of a wet milling technique using lysozyme as a surface stabilizer to some poorly soluble drugs. However, in this case, since the surface stabilizer is a protein, there are many restrictions in drying and accordingly only the preparation in liquid phase is disclosed.

US Patent Application Publication No. 2002/0168402 discloses a method for preparing nanoparticle using piston gap homogenization. However, in order to use piston gap homogenization, a pretreatment process using jet mill or hammer mill for grinding particle into uniform size is required. In addition, because this process is not available for highly viscose solution, it should be performed in a state where the concentration of active gradient is low.

As another conventional method, there is a recrystallization technique which provides fine particles of an active ingredient by changing the environment of a solution containing the active ingredient dissolved therein to cause the precipitation or crystallization of solute. The recrystallization technique can be practiced in two different ways: the one being comprised of dissolving a therapeutic agent in a suitable solvent and lowering the temperature, thereby changing the solubility of the therapeutic agent to precipitate particles; and the other being comprised of adding antisolvent to a solution containing the therapeutic agent dissolved therein, thereby decreasing the dissolving ability of the solvent to precipitate particles. However, most of such recrystallization techniques usually require use of organic solvent harmful to human, and flocculation or coagulation of the particles in wet condition occurs during a drying process after filtration of the precipitated particles. As a result, the final particles may not be uniform in size.

US Patent Application Publication No. 2003/0104068 A1 discloses a method for preparing fine particles by dissolving a polymer in an organic solvent, dissolving or dispersing a protein drug therein, rapidly cooling the solution to ultra-low temperature for solidification, and lyophilizing the product to provide fine powder. In this case, however, the protein drug may be denatured by the contact with an organic solvent, and the process needs the rapid cooling and lyophilizing processes and thus it is not economical.

In addition, there are techniques of reducing particle size by using emulsification. Such emulsifying methods are commonly used in cosmetic field, and provide fine particles by melting poorly water-soluble substances by heat or dissolving them in an organic solvent, and adding the melted or dissolved substances to an aqueous solution containing a surfactant dissolved therein, with stirring at high speed or with sonication to disperse the added substances. However, in this case, a step for removing water is required to provide fine particles in powder form, and many restrictions are generated during the water removal step. Furthermore, when an organic solvent is used to dissolve the poorly water-soluble substance, there always is a concern to the residual organic solvent harmful to human.

US Patent Application Publication No. 2004/0067251 A1 discloses a method for preparing fine particles by dissolving an active ingredient in an organic solvent and spraying the resulting solution into an aqueous solution containing a surfactant dissolved therein. This method uses an organic solvent, and since the prepared particles exist in an aqueous phase, a drying process is required for removing water used as solvent, to provide the particles in powder form. During the drying process, however, the coagulation of the particles occurs and thus it is hard to re-disperse them in nanoscale size.

Recently, many attempts have been made to use a supercritical fluid in preparing amorphous or nanoscale particles. Supercritical fluid is a fluid existing in liquid form at a temperature higher than its critical temperature and under pressure higher than its critical pressure. Commonly used supercritical fluid is carbon dioxide. As one of the methods using a supercritical fluid in preparing nanoparticles, rapid expansion of a supercritical solution ("RESS," hereinafter) has been known [Tom et al. *Biotechnol. Prog.* 7(5):403-411. (1991); U.S. Pat. Nos. 6,316,030 B1; 6,352,737 B1; and 6,368,620 B2]. According to this method, a target solute is firstly dissolved in a supercritical fluid, and then the supercritical solution is rapidly sprayed into a relatively low-pressure condition via nozzle. Then, the density of the supercritical fluid rapidly falls down. As a result, the ability of the supercritical fluid to solubilize the solute is also rapidly reduced, and the solute is formed into very fine particles or crystallines.

Other techniques using a supercritical fluid include a gas-antisolvent recrystallization ("GAS," hereinafter) [Debenedetti et al. *J. Control. Release* 24:27-44. (1993); WO 00/37169]. This method comprises dissolving a therapeutic agent in a conventional organic solvent to prepare a solution and spraying the solution through a nozzle into a supercritical fluid serving as an antisolvent. Then, rapid volume expansion occurs due to the contact between the solution and the supercritical fluid. As a result, the density and dissolving capacity of the solvent decrease, thereby causing extreme supersaturation and forming seeds or particles of the solute.

U.S. Pat. No. 6,630,121 discloses a method for preparing fine particles by nebulizing a solution containing active ingredients to fine particles by using a supercritical fluid, and drying the resulted particles with a dry gas. This method can be used regardless of the solubility of the active ingredients to the supercritical fluid. WO 02/38127 A2 discloses a method using SEDS (Solution Enhanced Dispersion by Supercritical fluids) technique for preparing fine particles of active ingredients and coating the resulted fine particles with an additive such as a polymer. Furthermore, U.S. Pat. No. 6,596,206 B2 discloses a technique of preparing fine particles of active ingredients by dissolving the active ingredients in an organic solvent and applying an ultrasonic wave to the resulted solution so that the solution can be sprayed in a form of fine particles into a supercritical fluid.

However, the prior arts using supercritical fluid have problems in uniformity between the production batches and in commercial production. In order to resolve such problems in the prior techniques using supercritical fluid, the methods using a supercritical fluid for preparing nano-powder of active ingredient wherein solid fat or the like is used as a solvent were suggested in Korean Patent Application Publication Nos. 2005-0054819, 2007-0107879 and 2007-0107841.

DETAILED DESCRIPTION OF THE INVENTION

Technical Purpose

The present invention seeks to solve the above-mentioned problems of the prior arts. In particular, the present invention can overcome the limitation of difficulty in preparing particles having a size smaller than micrometer-scale in traditional dry grinding process, and can solve the problem of particle growth and size-up during water removal step after grinding step due to the use of a lot of water in traditional wet grinding process. In addition, the present invention is to provide a method for preparing nanoparticles easily and effectively, even in the case of active ingredients having relatively low water solubility.

Technical Means

Accordingly, the present invention provides a method for preparing nanoparticle powder of active ingredient, comprising: uniformly mixing saccharide as an anti-coagulation agent; biocompatible polymer and/or surfactant; and active ingredient in the presence of water, drying the mixture, and grinding the dried mixture.

For example, a method for preparing nanoparticle powder of the present invention may be preferably performed through, but not limited thereto, the following steps:

(1) dissolving water-soluble saccharide as an anti-coagulation agent by using a minimum amount of water for its dissolution;

(2) adding biocompatible polymer and/or surfactant to the aqueous solution of saccharide obtained in step (1) and then mixing them uniformly;

(3) adding an active ingredient to the mixture obtained in step (2), and making the mixture in a homogeneous paste form and drying it; and (4) continuously milling the dried mixture obtained in step (3) by using one or more of various milling machines.

In the method for preparing nanoparticle according to the present invention, the active ingredient is a material that exhibits physiological activity in, for example, medicinal products, functional foods, cosmetics and the like. Preferably, the active ingredient is one or more selected from the group consisting of physiologically active organic compounds, organometallic compounds, natural extracts, peptides, proteins and polysaccharides. There is no special limitation to its state at room temperature such as solid phase or liquid phase, and its electrical form such as neutral or ionic form.

The term, "nanoparticle(s)" used herein refers to particle(s) wherein 90% or more of the particles have an average particle size of 5 μm or less, preferably 2 μm or less, more preferably 1 μm or less, still more preferably 0.5 μm or less.

In the present invention, the saccharide used as an anti-coagulation agent is of a concept including monosaccharide compounds, disaccharide compounds, polysaccharide compounds and sugar alcohols, particularly including glucose, lactose, mannitol, sucrose, xylitol, chitosan, starch fiber and the like.

The biocompatible polymer and/or surfactant useful in the present invention may be those used in medicinal products, foods and cosmetics, and there is no limitation to the electrical form such as ionic or nonionic, and the state at room temperature such as liquid phase, wax phase or solid phase.

There is no limitation to the scope of biocompatible polymer and surfactant that may be used in the present invention. Any known biocompatible polymer and surfactant or novel ones useful in preparing nanoparticle of active ingredient may be applied to the invention. Examples of biocompatible polymer may include, but not limited to, gelatin, casein, dextran, gum arabia, tragacanth gum, polyethylene glycol, carboxymethyl cellulose, hydroxypropyl cellulose, hydroxypropyl methylcellulose, methylcellulose, hydroxyethyl cellulose, hydroxypropyl methylcellulose phthalate, noncrystalline cellulose, polyvinyl alcohol, polyvinyl pyrrolidone, poloxamers, Eudragit®, lysozyme, albumin and the like. Examples of surfactant may include, but not limited to, cetyl pyridinium chloride, phospholipids, fatty acid, benzalkonium chloride, calcium stearate, glycerin esters of fatty acid, fatty alcohol, cetomacrogol, polyoxyethylene alkyl ethers, sorbitan esters, polyoxyethylene castor oil derivatives, polyoxyethylene sorbitan fatty acid esters, dodecyl trimethyl ammonium bromide, polyoxyethylene stearate, sodium lauryl sulfate, sucrose fatty acid ester, PEG-cholesterol, PEG-vitamin E and the like. Each of the above examples may be used alone or in combination with other(s).

According to one embodiment of the present invention, the saccharide to be used as an anti-coagulation agent is used in an amount of 0.5 to 5 parts by weight to 1 part by weight of active ingredient to be added in the following step. The saccharide is added to a reactor and then a small amount of water just for dissolving the saccharide completely, for example, 0.5 to 10 ml per 1 g of saccharide is added thereto. More specifically, 0.5 ml of water to 1 g of sucrose, 5 ml of water to 1 g of lactose, 1 ml of water to 1 g of glucose, 5.5 ml of water to 1 g of mannitol, 1.5 ml of water to 1 g of xylitol and 0.8 ml of water to 1 g of xylose may be used. After water is added to saccharide, the mixture is heated to 40 to 70° C. in order to completely dissolve the saccharide.

According to one embodiment of the present invention, the biocompatible polymer and/or surfactant is used in an amount of 0.01 to 10 parts by weight per 1 part by weight of active ingredient. For example, to an aqueous saccharide solution obtained as above, 0.01 to 10 parts by weight of biocompatible polymer and/or surfactant is added per 1 part by weight of active ingredient to be added in the following step, and then dissolved or mixed uniformly at 40 to 70° C. Active ingredient is added thereto, and then mixed uniformly by using a kneader. As a kneader, any type such as roller-type, arm-type or the like may be used as long as it can provide uniform mixing.

The mixture of saccharide—biocompatible polymer and/or surfactant—active ingredient obtained as such is dried to make its water content be 0.1 to 15% by weight, preferably 0.5 to 7% by weight based on the weight of solids other than water. There is no special limitation to the dry type.

Content of water in the dried resulting mixture may have a critical effect on the efficiency of the following grinding process, depending on the type of active ingredient. Generally, when melting point of active ingredient is high, higher water content is more advantageous for the grinding process, and when melting point of active ingredient is low, lower water content is more advantageous for the grinding process. However, if the water content is too high (for example, greater than 15% by weight), the viscosity of mixture to be ground is lowered and shearing force is not applied sufficiently during the grinding process, and accordingly the grinding efficiency may be lowered. On the other hand, if the water content is too low (for example, less than 0.1% by weight), too much torque is applied to the grinding machine and the grinding is not readily performed, and in case of roll mill, uniform grinding may be difficult. Because of such problems, it may be required to check the water content of the mixture after drying, and if water supplement is needed, add water before the grinding process, and conduct a granulation process. Such further added water may absorb large amount of heat generated during the grinding process and may reduce abrasion of the grinding device and a contamination thereby.

The dried mixture is then subject to a grinding process, preferably repetitive or continuous grinding process. In the grinding process, the ingredients constituting the mixture, particularly the active ingredient, biocompatible polymer and/or surfactant, are coagulated by crushing and then ground by shearing force. In this case, the saccharide used as anti-coagulation agent facilitates the repetitive grinding and consequently prepares nanoparticles of active ingredient more efficiently. Any device may be used without limitation in such grinding process as long as it can perform crushing and grinding simultaneously. In particular, if the continuous grinding process is performed by using an extruder, roll mill, rod mill or the like, nano-scale particles can be prepared more efficiently.

Generally, the grinding process is performed at 90° C. or less, preferably 60° C. or less, more preferably 40° C. or less, and still more preferably 30° C. or less. If the grinding process is performed at low temperature, denaturation of active ingredient by heat may be prevented, crystalline particle may maintain its crystallinity, and re-coagulation of the prepared particles may also be prevented effectively.

According to another embodiment of the present invention, the nanoparticle powder of active ingredient may be prepared by: making nanoparticles of saccharide as an anti-coagulation agent with biocompatible polymer and/or surfactant, uniformly mixing the nanoparticles with active ingredient, and grinding the mixture. In this method, after the step of making nanoparticles of saccharide as an anti-coagulation agent with biocompatible polymer and/or surfactant, the steps of mixing with active ingredient and grinding are same as explained above. In addition, after making nanoparticles of saccharide with biocompatible polymer and/or surfactant, the active ingredient and a small amount of water is uniformly mixed, by which the water content of the resulting mixture may be adjusted to 0.1 to 15 wt % based on the weight of solids.

Such a nanoparticle mixture of anti-coagulation agent may be prepared by using the processes disclosed in, for example, Korean Patent Application Publication Nos. 2005-0054819, 2007-0107879 and 2007-0107841. Specifically, under high speed agitation using a homo-mixer, an aqueous solution containing an anti-coagulation agent dissolved therein is added to a solution in which biocompatible polymer and/or surfactant were dissolved together with solid fat by heating to 70° C., and the resulting mixture is emulsified. The emulsification is considered to occur when a uniformly mixed solution is formed without phase separation of oil phase of solid fat from aqueous solution layer. When the mixture is emulsified sufficiently, it is slowly cooled to 50° C. or less, poured into a cooling plate or SUS tray to allow to solidify. Water is then removed by a drying process under reduced pressure, and the solid fat is removed by using supercritical fluid to provide nanoparticles of anti-coagulation agent.

Solid solvent (also referred to as "solid fat") means a compound that maintains solid phase at room temperature, i.e., 30° C. or less, and has a relatively low melting point of 30 to 150° C., preferably 30 to 90° C. and a high solubility in supercritical fluid. Its examples are disclosed in Korean Patent Application Publication No. 2005-0054819. Specifically, the solid solvent may be one or more selected from the group consisting of C10~C22 saturated fatty acids, and esters and alcohols thereof; mono- or di-glycerides having C10~C22 saturated fatty acid group; C16 or more hydrocarbons; fatty acid-reduced compounds of C10~C22 tri-glycerides; C6~C22, preferably C6~C10 linear or branched diol compounds such as 1,6-hexanediol; and mixtures thereof.

Effects of the Invention

According to the present invention, because of the existence of saccharide in a particle size of tens of micrometers or less, the limitation of difficulty in preparing particles having a size smaller than micrometer-scale in traditional dry grinding process can be overcome. In addition, the problem of particle growth and size-up during water removal step after grinding step due to the use of a lot of water in traditional wet grinding process can be solved. Furthermore, nanoparticles can be prepared easily and effectively even in the case of active ingredients having relatively low water solubility.

MODE FOR CARRYING OUT THE INVENTION

The present invention is explained in detail through the following examples.

However, the scope of the present invention is not limited thereto.

EXAMPLE 1

Figure 1:
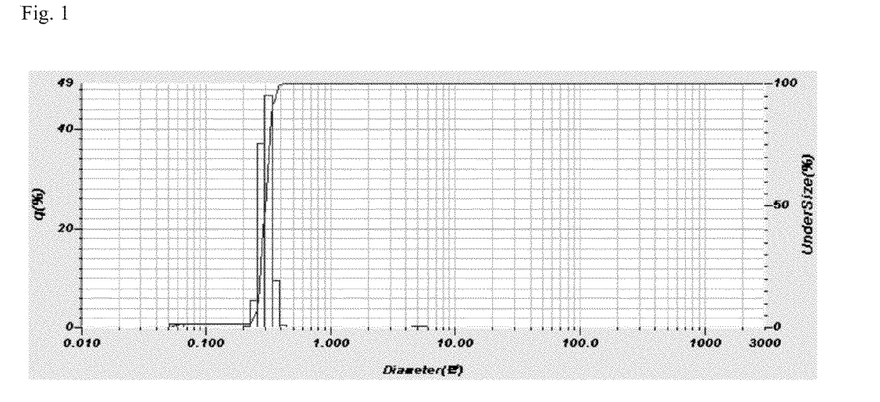
FIG. 1 is a particle size distribution analysis graph of phytosterol nanoparticles prepared in Example 1.

30 g of sucrose was added to 15 ml of water and slowly stirred at room temperature for 2 hours to dissolve it completely, and then 6 g of sucrose fatty acid ester and 1.5 g of polysorbate (80) as surfactants were added thereto. The resulting mixture was stirred at 60° C. for 20 minutes to prepare a uniform mixture. 30 g of phytosterol as an active ingredient was added to the mixture, and the resulting mixture was stirred at room temperature for 1 hour to obtain a mixture in the form of paste. The resulting mixture was dried under reduced pressure to obtain 65 g of dried powder. 2.5 ml of water was added to the dried powder and granulation was conducted. Grinding process using roll mill was then performed at room temperature 30 times. The resulting powder was dried under reduced pressure to obtain 63 g of nanoparticles comprising phytosterol. The powder was stirred at 60 to 70° C. for 30 minutes and then at room temperature for 1 hour, and the particle size distribution was analyzed by using Horiba LA950. The analysis results are as follows (unit: micrometer) and the particle size distribution analysis graph is shown in FIG. 1.

| D10 | D50 | D90 | Mean |
| --- | --- | --- | --- |
| 0.2618 | 0.3018 | 0.3392 | 0.3153 |

EXAMPLE 2

Figure 2:
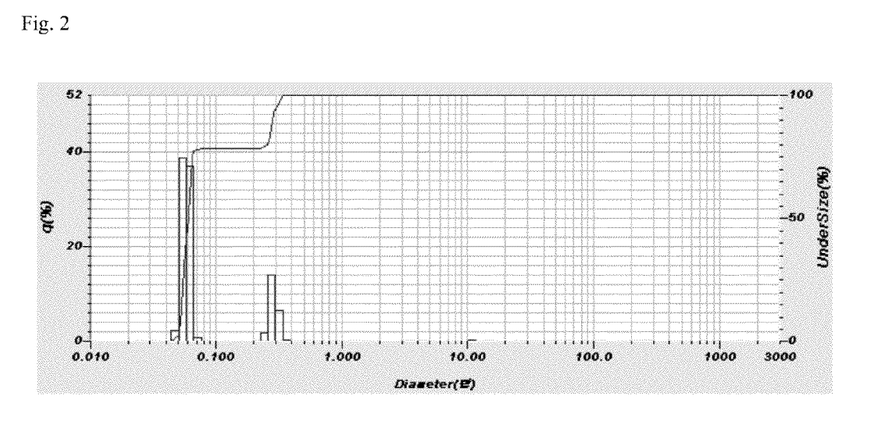
FIG. 2 is a particle size distribution analysis graph of coenzyme Q10 nanoparticles prepared in Example 2.

40 g of sucrose was added to 30 ml of water and slowly stirred at room temperature for 2 hours to dissolve it completely, and then 10 g of sucrose fatty acid ester and 0.5 g of polysorbate (80) as surfactants were added thereto. The resulting mixture was stirred at 60° C. for 20 minutes to prepare a uniform mixture. 10 g of coenzyme Q10 as an active ingredient was added to the mixture, and the resulting mixture was stirred at 60° C. for 20 minutes, and then kneaded at room temperature for 30 minutes to obtain a mixture in the form of paste. The resulting mixture was dried under reduced pressure at room temperature to obtain 63 g of dried powder (water content: about 5%). Grinding process using roll mill was then performed at room temperature 20 times. The resulting powder was dried under reduced pressure to obtain 59 g of nanoparticles comprising coenzyme Q10. The powder was stirred at 60 to 70° C. for 30 minutes and then at room temperature for 1 hour, and the particle size distribution was analyzed by using Horiba LA950. The analysis results are as follows (unit: micrometer) and the particle size distribution analysis graph is shown in FIG. 2.

| D10 | D50 | D90 | Mean |
|---|---|---|---|
| 0.0522 | 0.0601 | 0.2866 | 0.12628 |

EXAMPLE 3

Figure 3:
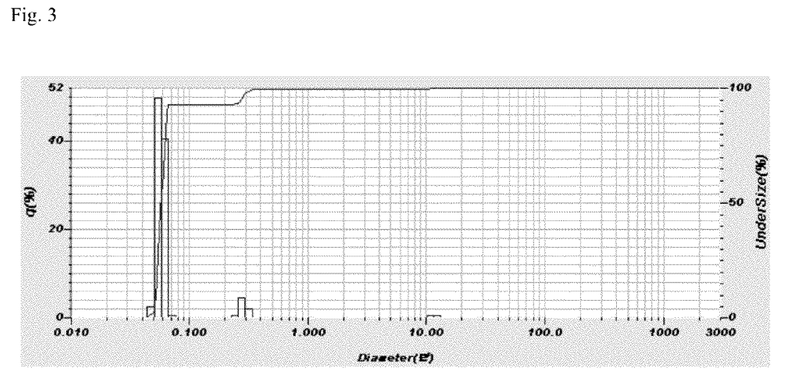
FIG. 3 is a particle size distribution analysis graph of octacosanol nanoparticles prepared in Example 3.

12 g of sucrose was added to 9 ml of water and slowly stirred at room temperature for 2 hours to dissolve it completely, and then 3 g of sucrose fatty acid ester and 0.15 g of polysorbate (80) as surfactants were added thereto. The resulting mixture was stirred at 60° C. for 20 minutes to prepare a uniform mixture. 3 g of octacosanol as an active ingredient was added to the mixture, and the resulting mixture was stirred at 80 to 85° C. for 20 minutes, and then kneaded at room temperature for 30 minutes to obtain a mixture in the form of paste. The resulting mixture was dried under reduced pressure at room temperature to obtain 18.4 g of dried powder. 1 ml of water was added to the dried powder and granulation was conducted. Grinding process using roll mill was then performed at room temperature 30 times to obtain 17.3 g of nanoparticles comprising octacosanol. The particle size distribution was analyzed by using Horiba LA950. The analysis results are as follows (unit: micrometer) and the particle size distribution analysis graph is shown in FIG. 3.

| D10 | D50 | D90 | Mean |
|---|---|---|---|
| 0.0518 | 0.0578 | 0.0660 | 0.1363 |

EXAMPLE 4

20 g of sucrose was added to 15 ml of water and slowly stirred at room temperature for 2 hours to dissolve it completely, and then 5 g of sucrose fatty acid ester and 0.5 g of polysorbate (80) as surfactants were added thereto. The resulting mixture was stirred at 60° C. for 1 hour to prepare a uniform mixture. 10 g of tyrosine as an active ingredient was added to the mixture, and the resulting mixture was stirred at 60° C. for 1 hour to obtain a mixture in the form of paste. The resulting mixture was dried under reduced pressure at room temperature to obtain 34 g of dried powder. 2.5 ml of water was added to the dried powder and granulation was conducted. Grinding process using roll mill was then performed at room temperature 20 times to obtain 33 g of nanoparticles comprising tyrosine.

EXAMPLE 5

Figure 4:
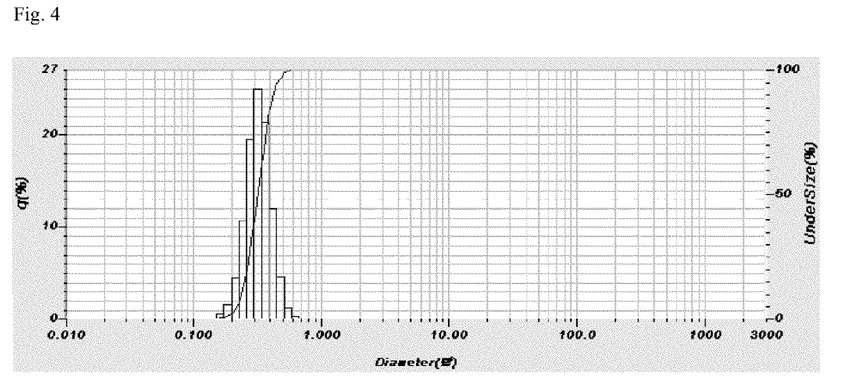
FIG. 4 is a particle size distribution analysis graph of phytosterol nanoparticles prepared in Example 5.

30 g of sucrose was added to 15 ml of water and slowly stirred at room temperature for 2 hours to dissolve it completely, and then 15 g of polyglycerin fatty acid ester and 1.5 g of sucrose fatty acid ester as surfactants were added thereto. The resulting mixture was stirred at 60° C. for 20 minutes to prepare a uniform mixture. 30 g of phytosterol as an active ingredient was added to the mixture, and the resulting mixture was stirred at room temperature for 1 hour to obtain a mixture in the form of paste. The resulting mixture was dried under reduced pressure to obtain 76 g of dried powder. 2.5 ml of water was added to the dried powder and granulation was conducted. Grinding process using roll mill was then performed at room temperature 30 times, and the resulting powder was dried under reduced pressure to obtain 73 g of nanoparticles comprising phytosterol. The powder was stirred at room temperature for 30 minutes, and then stirred and dispersed at 70° C. or higher for 30 minutes. The particle size distribution of the dispersion was analyzed by using Horiba LA950. The analysis results are as follows (unit: micrometer) and the particle size distribution analysis graph is shown in FIG. 4.

| D10 | D50 | D90 | Mean |
|---|---|---|---|
| 0.2369 | 0.3193 | 0.4245 | 0.3259 |

EXAMPLE 6

Figure 5:
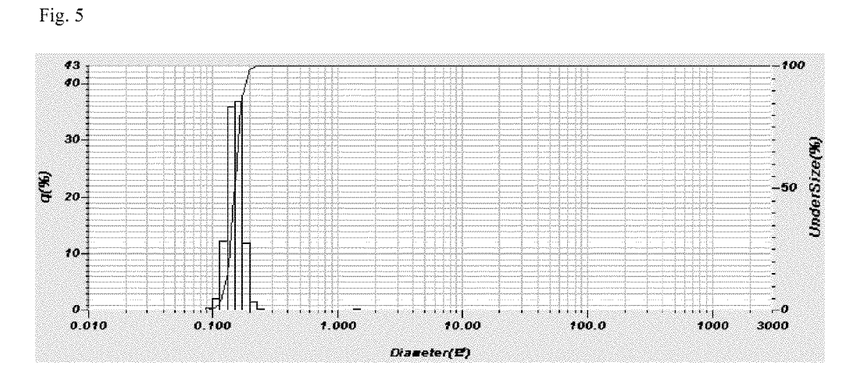
FIG. 5 is a particle size distribution analysis graph of coenzyme Q10 nanoparticles prepared in Example 6.

40 g of sucrose was added to 30 ml of water and slowly stirred at room temperature for 2 hours to dissolve it completely, and then 20 g of polyglycerol fatty acid ester (HLB 12) and 1 g of polyglycerin fatty acid ester (HLB 14) as surfactants were added thereto. The resulting mixture was stirred at 60° C. for 20 minutes to prepare a uniform mixture. 20 g of coenzyme Q10 as an active ingredient was added to the mixture, and the resulting mixture was stirred at 60° C. for 20 minutes, and then kneaded at room temperature for 30 minutes to obtain a mixture in the form of paste. The resulting mixture was dried under reduced pressure at room temperature to obtain 85 g of dried powder (water content: about 5%). Grinding process using roll mill was then performed at room temperature 20 times. The resulting powder was dried under reduced pressure to obtain 78 g of nanoparticles comprising coenzyme Q10. The powder was stirred at room temperature for 10 minutes and then at 38 to 43° C. for 30 minutes, and the particle size distribution was analyzed by using Horiba LA950. The analysis results are as follows (unit: micrometer) and the particle size distribution analysis graph is shown in FIG. 5.

| D10 | D50 | D90 | Mean |
|---|---|---|---|
| 0.1249 | 0.1503 | 0.1790 | 0.1536 |

EXAMPLE 7

40 g of sucrose was added to 30 ml of water and slowly stirred at room temperature for 2 hours to dissolve it completely, and then 10 g of sucrose fatty acid ester and 0.5 g of polysorbate (80) as surfactants were added thereto. The resulting mixture was stirred at 60° C. for 1 hour to prepare a uniform mixture. 10 g of calcium carbonate as an active ingredient was added to the mixture, and the resulting mixture was stirred at 60° C. for 1 hour to obtain a mixture in the form of paste. The resulting mixture was dried under reduced pressure at room temperature to obtain 60 g of dried powder. 2.5 ml of water was added to the dried powder and granulation was conducted. Grinding process using roll mill was then performed at room temperature 20 times to obtain 58 g of nanoparticles comprising calcium carbonate.

EXAMPLE 8

180 g of myristyl alcohol and 3 g of poloxamer (188) were mixed and the mixture was then heated to 70° C. to give a completely dissolved solution. Using a homomixer (Tokushu Kika, Mark II) at 4000 rpm, the resulting solution was slowly added to, and simultaneously mixed with, a solution of 18 g of lactose completely dissolved in 180 g of distilled water. The resulting solution was then cooled to 50° C. and poured into a stainless tray at room temperature and solidified, and then dried under reduced pressure. 195 g of the dried powder was placed in an extraction apparatus using supercritical fluid and myristyl alcohol was extracted and removed therefrom at 20° C. or lower under 70 to 90 atmospheric pressure to obtain 20 g of nanoparticles comprising lactose.

EXAMPLE 9

Figure 6:
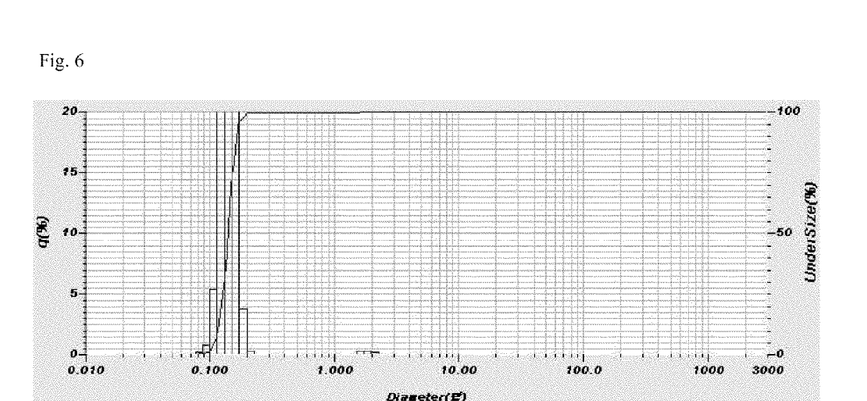
FIG. 6 is a particle size distribution analysis graph of fenofibrate nanoparticles prepared in Example 9.

10.5 g of the nanoparticles of the mixture of lactose and poloxamer (188) obtained in Example 8, 5 g of fenofibrate and 0.5 ml of distilled water were mixed uniformly using a household mixer. Grinding process using roll mill was then performed at room temperature 30 times. The resulting mixture was then dried under reduced pressure to obtain 15 g of nanoparticles comprising fenofibrate. The powder was stirred at room temperature for 10 minutes and then treated with ultrasonic wave for 1 minute. The particle size distribution was analyzed by using Horiba LA950. The analysis results are as follows (unit: micrometer) and the particle size distribution analysis graph is shown in FIG. 6.

| D10 | D50 | D90 | Mean |
| --- | --- | --- | --- |
| 0.1170 | 0.1397 | 0.1666 | 0.1505 |

EXAMPLE 10

Figure 7:
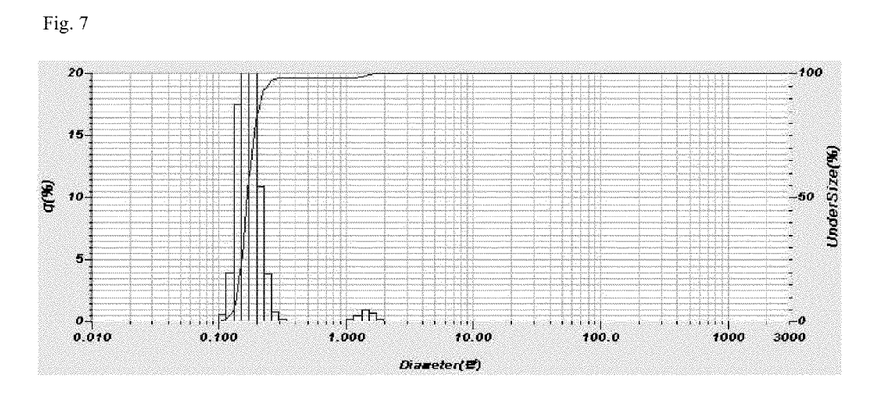
FIG. 7 is a particle size distribution analysis graph of itraconazole nanoparticles prepared in Example 10.

10.5 g of the nanoparticles of the mixture of lactose and poloxamer (188) obtained in Example 8, 5 g of itraconazole and 0.5 ml of distilled water were mixed uniformly using a household mixer. Grinding process using roll mill was then performed at room temperature 30 times. The resulting mixture was then dried under reduced pressure to obtain 15 g of nanoparticles comprising itraconazole. The powder was stirred at room temperature for 10 minutes and then treated with ultrasonic wave for 3 minutes. The particle size distribution was analyzed by using Horiba LA950. The analysis results are as follows (unit: micrometer) and the particle size distribution analysis graph is shown in FIG. 7.

| D10 | D50 | D90 | Mean |
| --- | --- | --- | --- |
| 0.1370 | 0.1681 | 0.2170 | 0.1994 |

EXAMPLE 11

Figure 8:
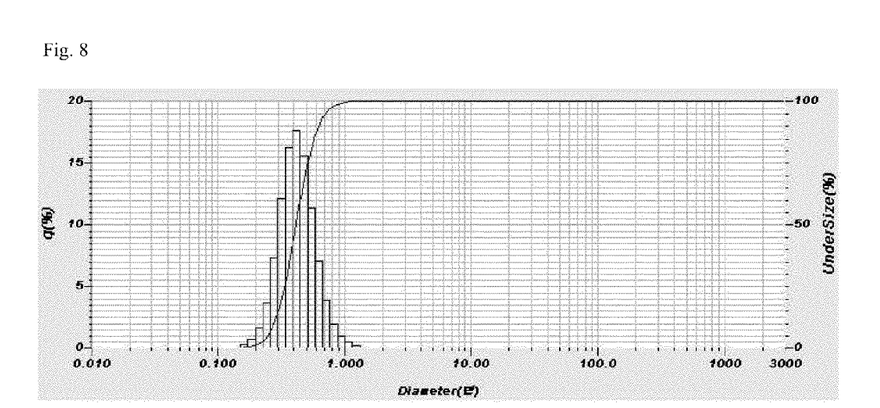
FIG. 8 is a particle size distribution analysis graph of megestrol acetate nanoparticles prepared in Example 11.

10.5 g of the nanoparticles of the mixture of lactose and poloxamer (188) obtained in Example 8, 5 g of megestrol acetate and 0.5 ml of distilled water were mixed uniformly using a household mixer. Grinding process using roll mill was then performed at room temperature 30 times. The resulting mixture was then dried under reduced pressure to obtain 15 g of nanoparticles comprising megestrol acetate. The powder was stirred at room temperature for 10 minutes and then treated with ultrasonic wave for 3 minutes. The particle size distribution was analyzed by using Horiba LA950. The analysis results are as follows (unit: micrometer) and the particle size distribution analysis graph is shown in FIG. 8.

| D10 | D50 | D90 | Mean |
| --- | --- | --- | --- |
| 0.2789 | 0.4150 | 0.6329 | 0.4403 |

EXAMPLE 12

Figure 9:
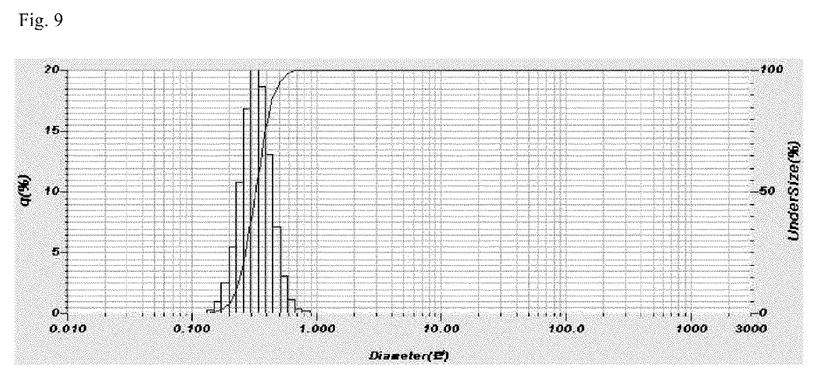
FIG. 9 is a particle size distribution analysis graph of naproxen nanoparticles prepared in Example 12.

10.5 g of the nanoparticles of the mixture of lactose and poloxamer (188) obtained in Example 8, 5 g of naproxen and 0.5 ml of distilled water were mixed uniformly using a household mixer. Grinding process using roll mill was then performed at room temperature 30 times. The resulting mixture was then dried under reduced pressure to obtain 15 g of nanoparticles comprising naproxen. The powder was stirred at room temperature for 10 minutes and then treated with ultrasonic wave for 3 minutes. The particle size distribution was analyzed by using Horiba LA950. The analysis results are as follows (unit: micrometer) and the particle size distribution analysis graph is shown in FIG. 9.

| D10 | D50 | D90 | Mean |
| --- | --- | --- | --- |
| 0.2288 | 0.3244 | 0.4599 | 0.3365 |

EXAMPLE 13

Figure 10:
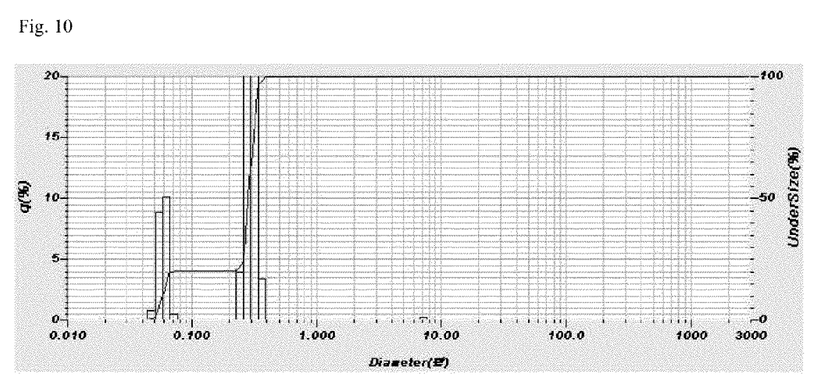
FIG. 10 is a particle size distribution analysis graph of talniflumate nanoparticles prepared in Example 13.

10.5 g of the nanoparticles of the mixture of lactose and poloxamer (188) obtained in Example 8, 5 g of talniflunate and 0.5 ml of distilled water were mixed uniformly using a household mixer. Grinding process using roll mill was then performed at room temperature 30 times. The resulting mixture was then dried under reduced pressure to obtain 15 g of nanoparticles comprising talniflunate. The powder was stirred at room temperature for 10 minutes and then treated with ultrasonic wave for 3 minutes. The particle size distribution was analyzed by using Horiba LA950. The analysis results are as follows (unit: micrometer) and the particle size distribution analysis graph is shown in FIG. 10.

| D10 | D50 | D90 | Mean |
| --- | --- | --- | --- |
| 0.0584 | 0.2851 | 0.3311 | 0.2584 |

EXAMPLE 14

90 g of lauric acid and 3 g of polyglycerin fatty acid ester were mixed and the mixture was then heated to 70° C. to give a completely dissolved solution. Using a homomixer (Tokushu Kika, Mark II) at 4000 rpm, the resulting solution was slowly added to, and simultaneously mixed with, a solution of 12 g of mannitol completely dissolved in 60 g of distilled water. The resulting solution was then cooled to 50° C. and poured into a stainless tray at room temperature and solidified, and then dried under reduced pressure. 100 g of the dried powder was placed in an extraction apparatus using supercritical fluid and lauric acid was extracted and removed therefrom at 15° C. or lower under 60 to 80 atmospheric pressure to obtain 14 g of nanoparticles comprising mannitol.

EXAMPLE 15

Figure 11:
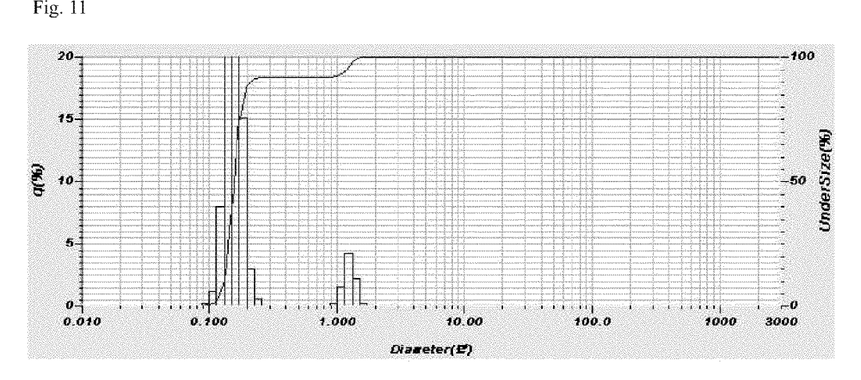
FIG. 11 is a particle size distribution analysis graph of coenzyme Q10 nanoparticles prepared in Example 15.

10 g of the nanoparticles of the mixture of mannitol and polyglycerin fatty acid ester obtained in Example 14, 2 g of coenzyme Q10 and 0.3 ml of distilled water were mixed uniformly using a household mixer. Grinding process using roll mill was then performed at room temperature 30 times. The resulting mixture was then dried under reduced pressure to obtain 14 g of nanoparticles comprising coenzyme Q10. The powder was stirred at room temperature for 10 minutes and then treated with ultrasonic wave for 3 minutes. The particle size distribution was analyzed by using Horiba LA950. The analysis results are as follows (unit: micrometer) and the particle size distribution analysis graph is shown in FIG. 11.

| D10 | D50 | D90 | Mean |
| --- | --- | --- | --- |
| 0.1317 | 0.1576 | 0.2128 | 0.2459 |

The invention claimed is:

1. A method for preparing a nanoparticle powder of an active ingredient, comprising:
uniformly mixing an anti-coagulating amount of a saccharide; a biocompatible polymer and/or a surfactant; and an active ingredient in the presence of water to form a wet mixture,
drying the wet mixture to form a dried mixture, and grinding the dried mixture.

2. The method according to claim 1, wherein the active ingredient is selected from the group consisting of physiologically active organic compounds, organometallic compounds, natural extracts, peptides, proteins and polysaccharides and combinations thereof.

3. The method according to claim 1, wherein the saccharide is selected from the group of monosaccharide compounds, disaccharide compounds, polysaccharide compounds and sugar alcohols and combinations thereof.

4. The method according to claim 1, wherein the biocompatible polymer is selected from the group consisting of gelatin, casein, dextran, gum arabia, tragacanth gum, polyethylene glycol, carboxymethyl cellulose, hydroxypropyl cellulose, hydroxypropyl methylcellulose, methylcellulose, hydroxyethyl cellulose, hydroxypropyl methylcellulose phthalate, noncrystalline cellulose, polyvinyl alcohol, polyvinyl pyrrolidone, poloxamer, eudragit, lysozyme and albumin and combinations thereof.

5. The method according to claim 1, wherein the surfactant is selected from the group consisting of cetyl pyridinium chloride, phospholipids, fatty acid, benzalkonium chloride, calcium stearate, glycerin esters of fatty acid, fatty alcohol, cetomacrogol, polyoxyethylene alkyl ethers, sorbitan esters, polyoxyethylene castor oil derivatives, polyoxyethylene sorbitan fatty acid esters, dodecyl trimethyl ammonium bromide, polyoxyethylene stearate, sodium lauryl sulfate, sucrose fatty acid ester, PEG-cholesterol and PEG-vitamin E and combinations thereof.

6. The method according to claim 1, wherein from 0.5 ml to 10 ml of water per 1 g of saccharide is used for mixing the saccharide, the biocompatible polymer and/or the surfactant, and the active ingredient.

7. The method according to claim 1, wherein, after drying the wet mixture, the dried mixture has a water content of 0.1 to 15 wt % based on the weight of solids other than water.

8. A method for preparing a nanoparticle powder of an active ingredient, comprising:
making nanoparticles of a saccharide as an anti-coagulation agent with a biocompatible polymer and/or a surfactant,
uniformly mixing the nanoparticles with the active ingredient to form a mixture, and grinding the mixture,
wherein, after making the nanoparticles of saccharide as an anti-coagulation agent with biocompatible polymer and/or surfactant and uniformly mixing the nanoparticles with active ingredient, the uniform mixture has a water content of 0.1 to 15 wt % based on the weight of solids.

9. The method according to claim 1, wherein, after the drying and before grinding, the dried mixture is granulated in the presence of water.

10. The method according to claim 1, wherein the grinding is performed by a continuous grinding process using an extruder, roll mill or rod mill.

* * * * *